United States Patent [19]

Hoffman

[11] 4,337,036
[45] Jun. 29, 1982

[54] ORTHOPEDIC PRESSURE APPLIANCE AND METHOD FOR CONTROLLING DEVELOPMENT OF THE MAXILLARY BONE

[76] Inventor: Carl S. Hoffman, 390 Crestwood Dr., Cheshire, Conn. 06410

[21] Appl. No.: 181,632

[22] Filed: Aug. 26, 1980

Related U.S. Application Data

[63] Continuation of Ser. No. 71,174, Aug. 31, 1979, abandoned.

[51] Int. Cl.$^3$ ................................................ A61C 7/00
[52] U.S. Cl. .......................................... 433/5; 433/6
[58] Field of Search ........................................ 433/6, 5

[56] References Cited

U.S. PATENT DOCUMENTS 2,983,046 5/1961 Jenkins ..................................... 433/5

Primary Examiner—Robert Peshock
Attorney, Agent, or Firm—Paul J. Sutton

[57] ABSTRACT

An Orthopedic Pressure Appliance is adapted to be retained in the mouth with resilient wires extending therefrom for attachment to a headcap by elastomeric means for urging the appliance against the maxillary teeth. The upper surface of the appliance has a posteriorly upward sloping flange for engaging the gingival third of the labial surfaces of the anterior teeth and a posteriorly upward sloping surface for supporting the incisive edges of the anterior teeth. The labial-buccal flange tapers downwardly and posteriorly away from the anterior portion thereof to prevent impingement on the gingiva and alveolus. A substantially flat and deep lower surface is provided to avoid entrapment of the mandibular anterior teeth.

6 Claims, 7 Drawing Figures

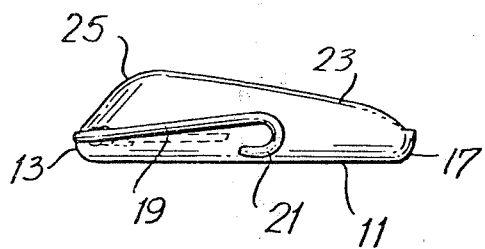
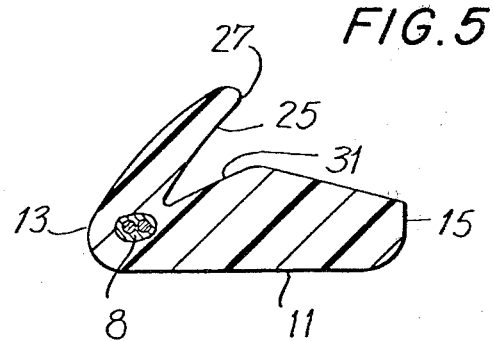
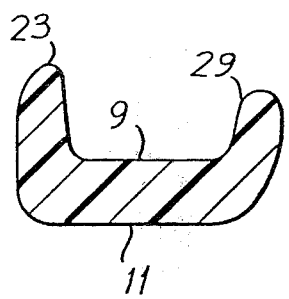
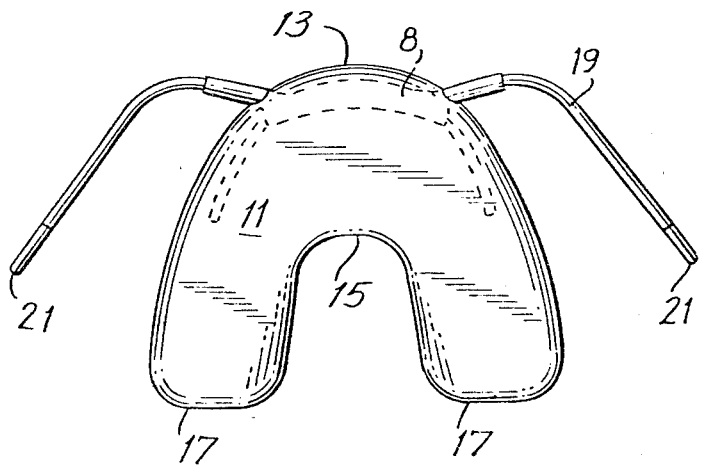

ORTHOPEDIC PRESSURE APPLIANCE AND METHOD FOR CONTROLLING DEVELOPMENT OF THE MAXILLARY BONE

This is a continuation of application Ser. No. 71,174, filed Aug. 31, 1979 and now abandoned.

BACKGROUND OF THE INVENTION

The instant invention relates to the field of dental devices utilized in treating the developing oro-facial complex by exerting orthopedic pressure so as to alter, control, and direct the vertical and horizontal growth of the maxillary bone. More specifically, the invention relates to such devices which include a body of plastic material conforming to a more or less ideal dental arch adapted to be retained in the mouth and resilient wires extending outside of the mouth through which pressure can be applied to the body by means of rubberbands or the like connected between the wires and a headcap worn by the patient.

Heretofore it has been a generally accepted practice to use devices formed of resilient material to guide or position errupted or errupting teeth. It has also been accepted practice to use devices or a combination of devices formed from metal, resilient resins, and hard resins both fixed to the teeth and/or easily removable by the patient to reposition the teeth so as to accomplish orthodontic tooth movement.

It is also known in the art to correct malaligned teeth by applying pressure upon the labial, and lingual surfaces of the teeth to urge their occlusive surfaces into a correct arch with the maxillary and mandibular teeth having a corrected relationship. One such device which includes a body retained in the mouth and having wires extending outside of the mouth for attachment to an elastic band is disclosed in U.S. Pat. No. 2,983,046 to Jenkins for a dental appliance. The Jenkins device includes flanges extending from its upper and lower surfaces for urging the upper and lower jaws into a position corresponding to proper alignment of the maxillary and mandibular teeth. Similar devices are disclosed in U.S. Pat. Nos. 2,882,612 and 2,880,509 to Strickler.

The orthopedic dental devices of the prior art which are directed to realignment of malaligned jaws suffer from several shortcomings in that they tend to move the incisal edges of the anterior teeth more lingually than the root apices. The flanges provided on such devices also hinder lateral development of the alveolus and frequently impinge on the gingiva thereby resulting in pain to the patient and requiring unscheduled adjustment visits to the treating dentist.

Prior art devices which have flanges on their upper and lower surfaces require that the mouth of the patient remain closed in order for them to be effective. This is both uncomfortable and inconvenient to the patient.

Some of the present concepts of facial development consider the formation of the long face syndrome, high mandibular angle, retrusive mandible, Class II facial pattern, to be the result of some occurrences in the naso-pharynx that cause the growing child to adopt a posture with the mandible dropped or hinged open. This results in an excessive vertical development of the maxillary complex. The combination of the hinged-open mandible swinging down and posteriorly and the excessive vertical growth of the maxilla results in the maxillary and mandibular anterior teeth failing to establish occlusal contact. The resulting overdevelopment of the alveolar processes leads to problems of appearance and occlusion that are extremely difficult and complex to correct in the fully grown patient, sometimes being of such a crippling character as to require surgical alteration of the bones and dental apparatus. Since the lower lip is attached to the mandible, it may also become trapped between the lower anterior teeth and the upper anterior teeth, and by its pressure, both working and postural, further distort facial development. The instant invention is intended to treat this problem while overcoming the limitations of the prior art discussed above.

SUMMARY OF THE INVENTION

Briefly the present invention relates to a method of controlling the vertical and horizontal growth of the maxillary bone of a person in the treatment of the developing oro-facial complex and an appliance for achieving the treatment. More specifically the invention relates to a method wherein pressure is applied only to the gingival third of the labial surfaces of the anterior teeth while supporting the incisal edges of the teeth on a posteriorly upwardly sloping surface through the use of an orthopedic pressure appliance which includes a body having the form of a dental arch, a pair of symmetric resilient wire prongs extending laterally in opposite directions and posteriorly therefrom, a ridge extending upwardly from the upper surface of the body and defining and upwardly posteriorly sloping flange surface adapted to engage the gingival third of the maxillary anterior teeth and having an upward posteriorly sloping upper surface in the anterior region for supporting the incisal edges of the teeth. Flanges are also provided to control lateral positioning with the flange portions adapted to engage the buccal surfaces of the posterior teeth sloping downwardly to prevent impingement on the gingiva. The body has a substantially flat lower surface with an anterior portion extending posteriorly along the anterior midline a distance sufficient to preclude the possibility of entrapment of the lower anterior teeth behind the body.

It is therefore an object of the invention to provide a method and orthopedic pressure appliance for interfering with the development of the face by altering the functional matrix so as to allow the natural growth of the face to bring about a correction of both vertical and horizontal abnormalities.

Another object of the invention is to permit the exertion of pressure against the maxillary anterior teeth to cause a bodily lingual movement of each tooth subject to such pressure while preventing a tipping at the incisal edge in excess of the lingual movement of the root.

A further object of the invention is to provide such an appliance which is supported in the lateral direction without impingement upon the gingiva.

A still further object of the invention is to provide such an appliance having a surface which can be engaged by the mandibular teeth without entrapment of said teeth.

Other and further objects of the invention will be apparent from the following drawings and description of a preferred embodiment of the invention in which like reference numerals are used to indicate like parts in the various views.

DESCRIPTION OF THE DRAWINGS

FIG. 4 is a side view of the preferred embodiment of the invention.

FIG. 5 is a sectional view of the preferred embodiment of the invention taken through line 5—5 in FIG. 2.

FIG. 6 is a sectional view of the preferred embodiment of the invention taken through line 6—6 of FIG. 2.

FIG. 7 is a bottom view of the preferred embodiment of the invention.

DESCRIPTION OF THE PREFERRED EMBODIMENT

Figure 1:
FIG. 1 is a perspective view of the preferred embodiment of the invention in its intended environment.

Referring now to FIG. 1 of the drawings there is shown an orthopedic pressure appliance in accordance with the invention retained in the mouth of a person and applying pressure to control the growth of the maxillary bone as a result of the tension exerted by elastic bands 3 connected between a headcap 5 and the appliance. The structure of the appliance will now be described in detail with reference to FIGS. 2 through 7 of the drawings.

The orthopedic pressure appliance of the invention includes a body or tray 7 in the basic shape of what is considered to be an ideal maxillary dental arch. The body 7 is preferably formed from a thermoplastic resilient material.

The body 7 has an upper surface 9, a lower surface 11, a labial-buccal surface 13, a lingual surface 15 and two pharyngeal surfaces 17. The labial-buccal surface 13 and the lingual surface 15 generally following the shape of the dental arch and are spaced from one another by the upper surface 9 and lower surface 11 of the body 7. The labial-buccal surface and the lingual surface are bridged at either of the posterior ends of the body 7 by the pharyngeal surfaces 17.

Figure 2:
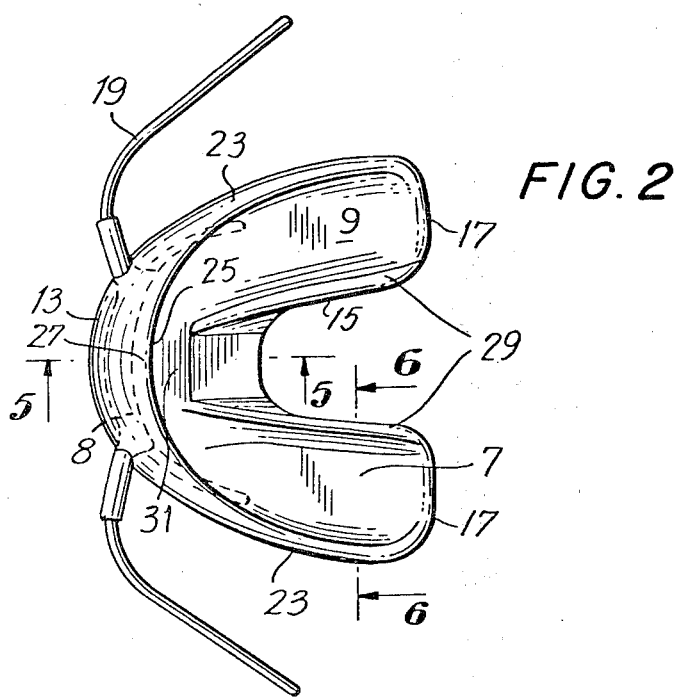
FIG. 2 is a plan view of the preferred embodiment of the invention.
Figure 3:
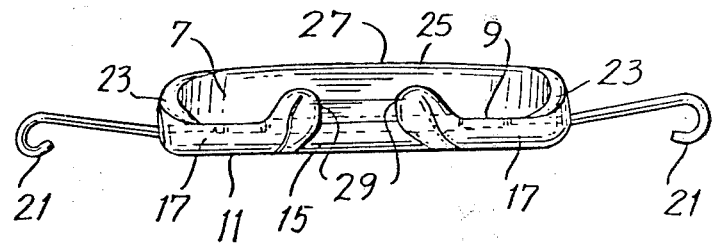
FIG. 3 is an end view of the preferred embodiment of the invention.

Embedded in and extending outwardly from the anterior midline, defined by section line 5—5 in FIG. 2 of the body 7 is a resilient metal wire bow 19. The bow 19 is bifurcated into two symmetric prong-like members extending away from the anterior midline and then posteriorly with the terminus of each prong being bent to form a hook 21 suitable for receiving and holding an end of one of the elastic bands 3. The prongs of the bow 19 are supported by an arcuate wire 8 embedded in the anterior portion of the body 7 and from which the prongs of the bow 19 extend.

Extending upwardly from the upper surface of the body 7 adjacent the labial-buccal surface 13 is a ridge 23 which defines an upwardly posteriorly sloping flange surface 25 (best seen in FIG. 5) at the anterior region of the body 7. The upper edge 27 of the flange 25 is at a height relative to the upper surface 9 of the body 7 so as to engage the gingival third of the maxillary anterior teeth when the incisive edges of the maxillary anterior teeth are in contact with the proximate upper surface of the body 7.

Extending upwardly from the upper surface 9 of the body adjacent each of the respective posterior regions of the lingual surface 15 are respective ridges 29. The ridges 29 are adapted to engage the lingual surfaces of the maxillary posterior teeth and/or the lingual mucosa. The anterior portion of the upper surface of the body 7 slopes posteriorly upwardly from the intersection of the upper surface 9 with the flange surface 25 merging with the ridges 29 to form an inclined supporting surface 31 (FIG. 5) for supporting the incisive edges of the maxillary anterior teeth. Hence as the edge 27 of the flange 25 is urged by the elastic bands 3 against the gingival third of the maxillary anterior teeth the inclined surface 31 prevents the incisive edges of the teeth from being moved more lingually than the root apices.

As the ridge 23 proceeds posteriorly and away from the anterior midline it slopes downwardly so that the posterior regions of the ridge 23 are shorter, that is lower in elevation, than is the anterior region of the ridge 23. This shortening of the labial-buccal flange, defined by the ridge 13, in the area of the bicuspids and molars eliminates impingement on the gingiva and alveolus. This allows unhindered lateral development of the alveolus and avoids pain to the patient of gingival impingement and adjustment visits required to relieve the pain.

Referring additionally to FIG. 7 of the drawings which shows the generally flat lower surface 11 on the underside of the body 7, it is seen that the distance between the labial-buccal surface 13 and the lingual surface 15 as measured along the anterior midline is approximately equal to one-half the overall length of the body 7 measured along the anterior midline, that is, the length measured from the intersection of the anterior midline with the labial-buccal surface 13 to a plane intersecting the rearwardmost points on the pharyngeal surfaces 17. The lower surface 11 of the body 7 serves as a biting surface for the mandibular teeth and provides a contacting surface suitable for even extremely retruded lower incisors. This arrangement avoids entrapment behind the body 7 of the lower anterior teeth which in the past has resulted in overgrowth of the alveolar process in the anterior area. The thickness of the body 7 enables it to also function as a posterior bite block to provide added support for the maxillary posterior teeth and bone. This increases the pressures used to prevent vertical growth.

The orthopedic pressure appliance of the present invention is constructed and designed so that it can be used in conjunction with fixed and attached orthodontic tooth-moving devices. After the desired attachments and/or brackets and/or arch wires designed to bring about tooth movement are in place, an orthopedic pressure appliance of appropriate size for the patient can be selected so as to encompass the attached, bonded, or cemented apparatus.

The use of a thermo-plastic resin in the formation of the body 7 allows modification of individual areas of the body 7 and its surfaces, ridges and flanges by application of heat or abrasives.

The present invention is designed to be used in conjunction with any of the commonly used headcaps known to the art. By altering the length of the prongs of the bow member 19 and the position of the attachment points 21 for the elastic bands 3, variations in direction of force can be achieved by the treating dentist so as to obtain the desired force direction. The size and number of elastic bands 3 can be altered to regulate the degree of force applied to the orthopedic pressure appliance. The number of hours of wear during each day is best determined by the treating dentist.

It is to be appreciated that modifications and alterations may be made to the preferred embodiment disclosed herein without departing from the spirit and scope of the invention which is defined in the following claims.

What is claimed is:

1. In an orthopedic pressure appliance comprising a body with a form approximating a dental arch with an anterior portion and two symmetric posterior portions extending therefrom and having a lingual surface, a labial-buccal surface, two pharyngeal surfaces bridging the adjacent respective posterior ends of said labial-buccal and lingual surfaces, an upper surface, a lower surface, and a pair of symmetrical wire prongs extending laterally in opposite directions and posteriorly from the labial edge of the anterior portion of said body, the improvement which comprises a first ridge extending upwardly from said upper surface adjacent said labial-buccal surface and defining a first flange surface upwardly posteriorly sloping at the anterior region extending laterally in opposite directions and posteriorly from the labial edge of the anterior portion of said body, the improvement which comprises a first ridge extending upwardly from said upper surface adjacent said labial-buccal surface and defining a first flange surface upwardly posteriorly sloping at the anterior region thereof and having there at an upper edge adapted to engage the gingival third or at least some of the maxillary anterior teeth, a second ridge and a third ridge each extending upwardly from said upper surface adjacent the respective posterior regions of said lingual surface and defining respective second and third flange surfaces adapted to engage the lingual surfaces of at least some of the maxillary posterior teeth or the lingual mucosa, the anterior region of said upper surface sloping posteriorly upwardly and merging with the respective anterior regions of said second and third ridges whereby the incisal edges of the teeth are precluded from being moved more lingually than the root apices as the first ridge is urged against the gingival third of the maxillary anterior teeth.

2. Apparatus according to claim 1 wherein the posterior regions of said first ridge are shorter than the anterior region thereof.

3. Apparatus according to claim 2 wherein said first ridge slopes downwardly from the anterior region thereof toward each posterior region thereof.

4. Apparatus according to claim 3 wherein said lower surface is generally flat.

5. Apparatus according to claim 4 wherein the distance between said labial-buccal surface and said lingual surface measured along the anterior midline of said body is approximately one-half the overall length of said body measured along the anterior midline.

6. A method of controlling the vertical and horizontal growth of the maxillary bone of a person in the treatment of the developing oro-facial complex comprising applying pressure to only the gingival third of the labial surfaces of at least some of the maxillary anterior teeth of the person and supporting the incisal edges of said anterior teeth on a posteriorly upwardly sloping surface thereby preventing the incisal edges of the teeth from being moved more lingually than the root apices as said pressure is applied to the gingival third of the labial surfaces of the maxillary teeth.

* * * * *